United States Patent [19]

Miyamura

[11] Patent Number: 4,926,502

[45] Date of Patent: May 22, 1990

[54] CORSET FOR ALLEVIATION OF LUMBAGO

[75] Inventor: Tetsuo Miyamura, Shiga, Japan

[73] Assignee: Wacoal Corp., Japan

[21] Appl. No.: 295,102

[22] Filed: Jan. 9, 1989

[51] Int. Cl.$^5$ ............................ A41C 1/00; A41C 1/08
[52] U.S. Cl. .................................................. 2/44; 2/2;
2/338; 450/132; 450/146; 450/116; 128/78
[58] Field of Search .................. 450/94, 109, 112, 114,
450/116, 132, 133, 4, 144, 143, 149; 2/338, 44, 2

[56] References Cited

U.S. PATENT DOCUMENTS

| | | | |
|---|---|---|---|
| 2,030,826 | 2/1936 | Schoebel | 450/114 |
| 2,132,033 | 10/1938 | Kapinas | 450/143 |
| 2,181,689 | 11/1939 | Bell | 2/44 X |
| 2,250,267 | 7/1941 | Lins | 2/44 X |
| 2,531,769 | 11/1950 | Desrochers | 450/132 |
| 2,537,781 | 1/1951 | Meyer | 450/132 |
| 2,730,096 | 1/1956 | Pease | 2/44 X |
| 3,307,535 | 3/1967 | Locke | 450/116 X |
| 3,310,053 | 3/1967 | Greenwood | 2/2 X |
| 3,921,222 | 11/1975 | Hollman | 2/2 |
| 4,022,197 | 5/1977 | Castigua | 450/116 X |
| 4,175,553 | 11/1979 | Rosenberg | 2/44 X |
| 4,292,263 | 9/1981 | Hanrahan et al. | 2/16 X |
| 4,384,372 | 5/1983 | Rector | 2/338 X |
| 4,404,820 | 9/1983 | Romaine | 62/530 |
| 4,592,358 | 6/1986 | Westplate | 272/119 X |
| 4,622,957 | 11/1986 | Curlee | 128/78 |
| 4,627,109 | 12/1986 | Carabelli et al. | 2/44 |
| 4,641,641 | 2/1987 | Strock | 2/2 X |
| 4,671,267 | 6/1987 | Stout | 128/156 |
| 4,703,750 | 11/1987 | Sebastian et al. | 2/338 X |
| 4,768,295 | 9/1988 | Ito | 36/28 |
| 4,833,730 | 5/1989 | Nelson | 2/44 |
| 4,836,194 | 6/1989 | Sebastian et al. | 2/338 X |

FOREIGN PATENT DOCUMENTS

| | | |
|---|---|---|
| 274996 | 6/1926 | United Kingdom . |
| 459236 | 6/1935 | United Kingdom . |
| 1520722 | 3/1977 | United Kingdom . |

Primary Examiner—Werner H. Schroeder
Assistant Examiner—Jeanette E. Chapman
Attorney, Agent, or Firm—Lowe, Price, LeBlanc, Becker & Shur

[57] ABSTRACT

A corset is provided for the alleviation of lumbago which has a non-stretchable section formed at a portion corresponding to the lumbar region in the center of a user's back with elastic core elements respectively connected to left and right side edges of the non-stretchable section, and a gel pad attached detachably to the non-stretchable section to deform and fill a gap between the user's lumbar back surface and the non-stretchable section during use.

7 Claims, 3 Drawing Sheets

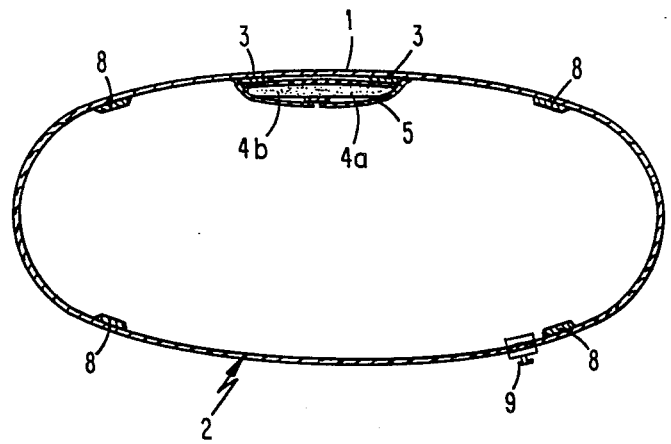
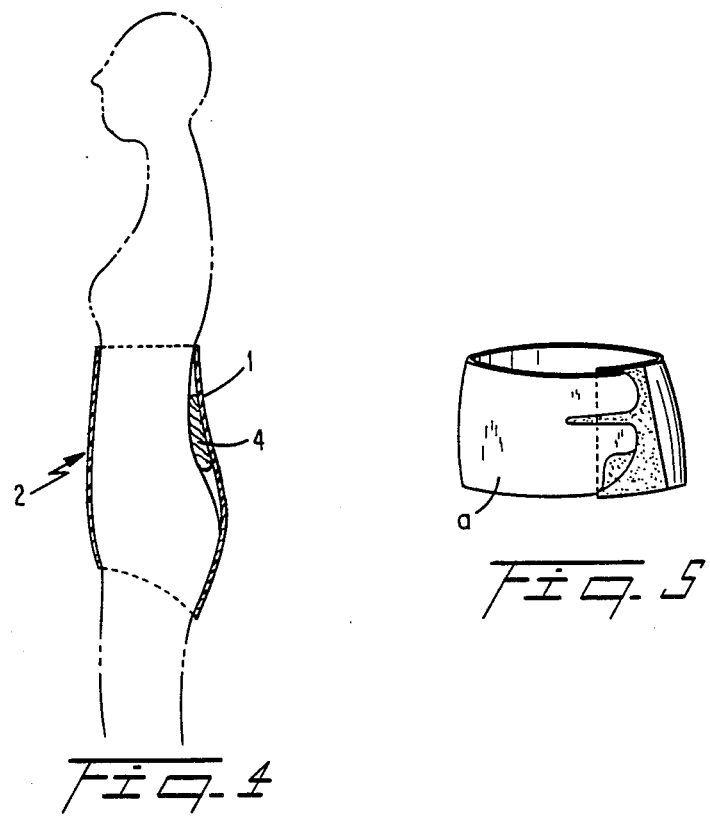

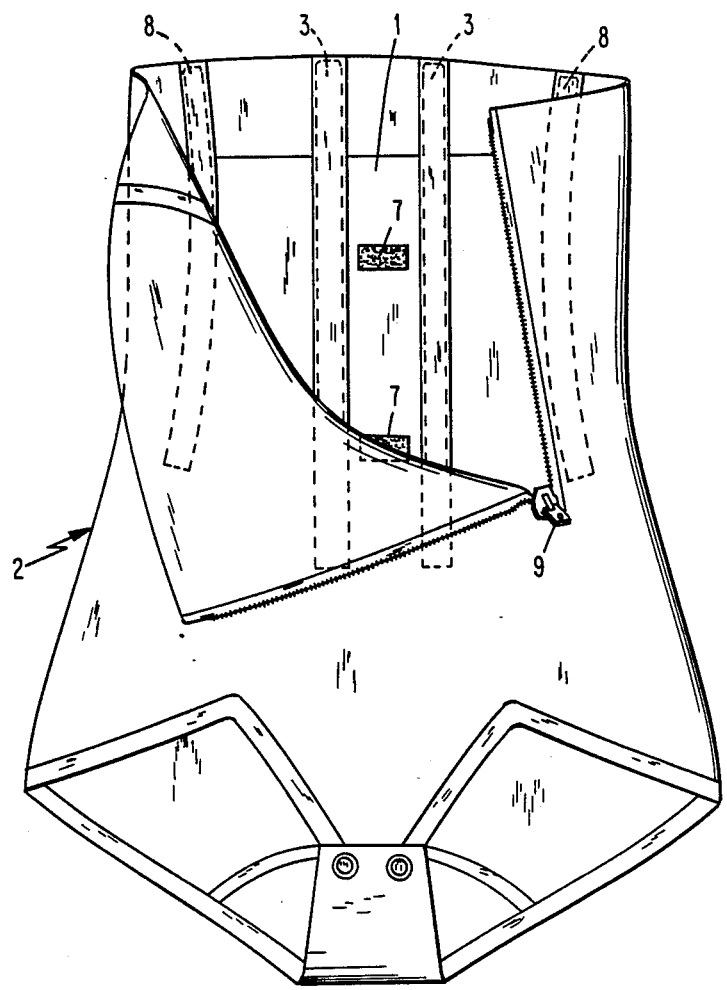
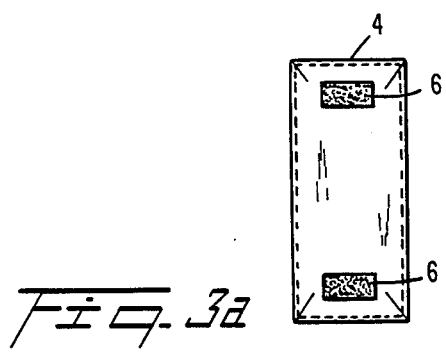

CORSET FOR ALLEVIATION OF LUMBAGO

FIELD OF THE INVENTION

The present invention relates to a corset to be used by a patient suffering from lumbago for alleviation thereof.

PRIOR ART

Generally, corsets of this type are advantageous for protection of the lumbar region of the back, for assisting the dorsal muscles and abdominal muscles to keep a healthy posture of the human body, thereby alleviating lumbago. To perform such a function, it is essential that the corset be tightly fitted to the patient's waist, particularly to the lumbar portion.

From this point of view, there has been heretofore proposed a corset for alleviation of lumbago comprising a stretchable belt (a), which is used by fastening at the waist tightly with a stretchable belt as illustrated in FIG. 5.

However, because each individual has his (or her) own physical figure or body shape, a problem exists in that differences in the; figures of individuals are not accommodated by the conventionally known corset, resulting in a poor fit between the corset and the waist of the user.

Even if a corset is tightly fitted to waist, there arises another problem that routine motions of waist necessary for daily life are restricted because a certain portion of the waist is fully fixed.

Moreover, according to routine motions such as bending forward, sitting, etc., the posture or position of user's waist varies frequently. As a result, the conventional lumbago-alleviating corset has a further disadvantage in that the fit of the corset to the waist is considerably affected by the routine motions with the passage of time, declining thereby the advantage of protecting lumbar and eventually bringing about a feeling of physical disorder in wearing the corset.

SUMMARY OF THE INVENTION

The present invention was made to solve the above-discussed problems and has an object of providing a corset for alleviation of lumbago in which routine motions of waist in daily life are not restricted, and which is fitted to the waist of a user regardless of differences in physical figure among individuals and of variation in posture or position according to the motions of waist, thereby achieving exact protection of the waist without causing the user a feeling of physical disorder in wearing the corset.

In order to accomplish the foregoing object, the corset for alleviation of lumbago according to the invention comprises a non-stretchable section which is formed at a portion which corresponds to the lumbar region in the center of the back of the user's body, elastic core materials which are respectively connected to left and right side edges of the non-stretchable section, and a gel pad which is detachably attached to the non-stretchable section.

In the corset of the above construction, the gel pad is interposed between the corset body and the user's lumbar region. Because of its fluidity, the gel pad can fill any gap formed between the corset body and lumbar region irrespective of difference in physical figure among individuals or in variation in posture according to motions of the waist. As a result, a tight fitness between the corset and lumbar is maintained, thereby protecting the lumbar and eliminating any feeling of physical discomfort in wearing the corset.

Other objects and features of the present invention will become apparent in the course of the following description taken with the accompanying drawings.

BRIEF DESCRIPTION OF THE DRAWINGS

In the drawings forming a part of the present application, with like reference numerals designated to like parts throughout the same.

FIG. 2 is a cross-sectional view thereof;

FIG. 3 is a front view of a lumbago-alleviating corset, according to another embodiment of the invention;

FIG. 4 is a longitudinal sectional view thereof when putting the corset on; and]

FIG. 5 is a front view of a known type of conventional corset.

DESCRIPTION OF THE PREFERRED EMBODIMENT

Several preferred embodiments of the present invention are now described hereinafter with reference to the accompanying drawings.

Figure 1:
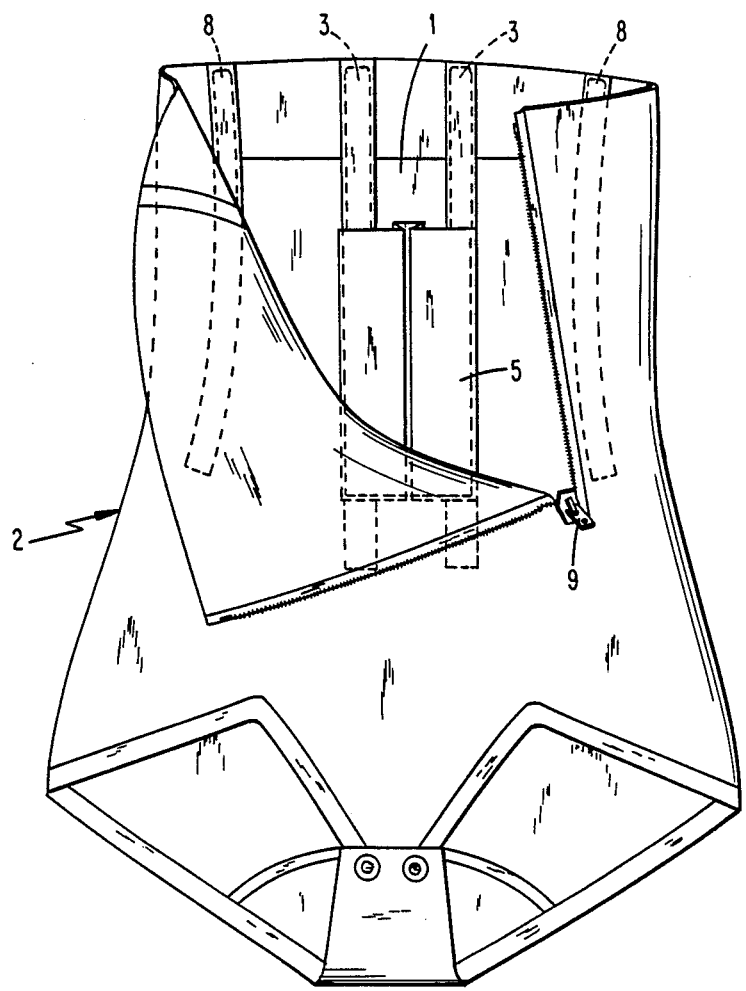
FIG. 1 is a front view of a lumbago-alleviating corset according to a preferred embodiment of the invention.
Figure 1A:
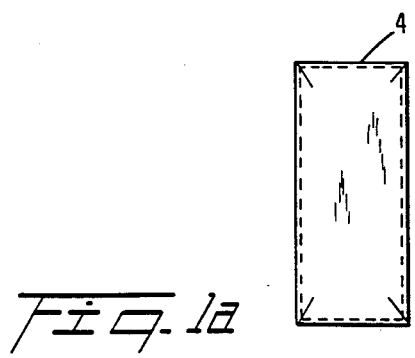

In FIGS. 1 and 2 both illustrate an embodiment of the invention, wherein the non-stretchable section is formed at a portion which corresponds to lumbar in the center of the back of the user's body. The non-stretchable section 1 can be made of a non-stretchable material such as non-stretchable cloth, film or the like. On the other hand, sections of the corset body 2 other than the non-stretchable section 1 can be made of a stretchable material.

Numerals 3, 3 are the elastic core elements which are respectively connected to left and right side edges of said non-stretchable section 1. Each of the elastic core elements 3, 3 can be formed into a plate of small width and made of a material such as synthetic resin or the like having predetermined hardness and elasticity. In view of the need for a tight fitness between the corset and waist, it is preferable that the elastic core elements 3, 3 be formed to be bent at the center thereof to each form a circular arc conforming to the physical figure of the user's waist so that the convex portions thereof face to the waist when the corset is worn. Each of the elastic core elements 3, 3 can be attached by inserting it in between the surface cloth and backing cloth of the corset body 2 and sewing up the peripheral edge portions. The elastic core elements 3, 3 are preferably located substantially at the left and right sides of the user's lumbar region to protect the lumbar area when he or she is putting the corset on.

Numeral 4 indicates the gel pad which is attached detachably to the non-strechable section 1. The gel pad 4 can be composed of a gel material 4a such as artificial element formed of silicon rubber similar in feel to human fat, a;nd is tightly enclosed within a packaging member 4b. For attaching the gel pad 4 detachably to the corset body 2, it is preferably that a bag 5 with its upper end open is sewn to the portion where the elastic core materials 3, 3 are attached, with the gel pad 4 then inserted into the bag 5, for example as illustrated in FIG. 2. The bag 5 is preferably made of elastic material with its outer edges sewn to the corset along the outer edges of the elastic portions 3, as best seen in FIGS. 1 and 2. It is also preferable that retainer pieces 6, 6, such as a so-called magic fastener, are sewn up to the back side of the gel pad 4 and loops 7, 7 to be mated with said retainers 6, 6 are sewn up to the corresponding portions of the non-stretchable section 1, as illustrated in FIG. 3. The gel pad 4 is interposed between the corset body 2 and waist when putting the corset on, and is freely deformed because of its fluidity. In this manner, tight fitness between the corset and lumbar surface is exactly kept, and the lumbar region is securely protected irrespective of differences in physical figures among individuals and in spite of variations in posture or position according to motions of the user's waist. Furthermore, a force directed toward the waist portion is given by the elastic core material 3, 3 and the non-stretchable section 1 disposed between the elastic core materials 3, 3 and, as a result, an even force is applied to the entire gel pad 4,1 which is also advantageous in view of the desired protection of waist portion.

Numerals 8, 8 indicate axillary core elements provided in another embodiment at desired portions such as sides of the corset body 2. The auxiliary core elements 8, 8, in the same manner as said elastic core elements 3, 3 can be formed into a plate of small width made of such a material as metal, synthetic resin or the like having proper hardness and elasticity. Each of the elastic core materials 3, 3 can be also attached by inserting it in between the surface cloth and backing cloth of the corset body 2 and sewing up peripheral edge portions.

Numeral 9 indicates a fastener for opening and closing of the corset body 2 when putting the corset on and off. In addition, it is also preferably that the front section of the corset body 2 is composed of strings in the form of lacing-up elements.

Since the corset for alleviation of lumbago according to the present invention is constructed as described above, when a user is wearing the corset of the invention his lumbar region is exactly protected for keeping healthy posture without restriction routine motions of waist in daily life, and lumbago is effectively alleviated. This is obtained irrespective of any differences in physical figure among individuals and of variations in posture or position according to the motions of the user's waist.

Furthermore, because of a force given to the waist portion by the non-stretchable section interposed between the elastic core materials, an even force is applied to the entire gel pad, which also results in satisfactory protection of waist as a whole.

While preferred embodiments have been described, variations, thereto will occur to those skilled in the art and such variations are regarded as comprehended within the scope of the present invention concepts which are delineated boy the following claims.

What is claimed is:

1. A corset for alleviation of lumbago, comprising:
   a non-stretchable section which is formed to be positioned at a portion which corresponds to the lumbar region in the center of the back of a human body;
   stretchable portions comprising elastic core materials which are respectively connected to left and right side edges of said non-stretchable section; and
   a gel pad disposed at said non-stretchable section so as to deformably fill any gap between the user's back and said non-stretchable section to provide improved back support to the user.

2. The corset according to claim 1, further comprising:
   means for detachably attaching said gel pad to said non-stretchable section.

3. The corset according to claim 2, wherein:
   said attachment means comprises cooperating detachable fastening elements disposed on a surface of said gel pad and an inside surface of said non-stretchable section.

4. The corset according to claim 1, further comprising:
   flexible containment means for detachably holding said gel pad against an inside surface of said non-strechable section.

5. The corset according to claim 4, wherein:
   said containment means comprises a bag open at an upper end to receive said gel pad therein, said bag being attached to an inner surface of the corset in correspondence with said non-stretchable section.

6. The corset according to claim 5, wherein:
   said bag is attached at its side edges to edges along which said stretchable portions are attached to said corset.

7. The corset according to claim 6, wherein:
   said bag comprises strechable elastic material.

* * * * *